US006309632B1

(12) United States Patent
Agosti

(10) Patent No.: US 6,309,632 B1
(45) Date of Patent: Oct. 30, 2001

(54) METHODS FOR TREATING HIV-INFECTED PATIENTS BY ADMINISTERING GM-CSF

(75) Inventor: Jan M. Agosti, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/067,926

(22) Filed: Apr. 28, 1998

(51) Int. Cl.[7] .................................................. A61K 45/00
(52) U.S. Cl. ...................... 424/85.1; 424/85.2; 514/45; 514/49; 514/50; 514/235.5
(58) Field of Search ................................ 424/85.1, 85.2; 514/2, 616, 235.5, 45, 49, 50

(56) References Cited

U.S. PATENT DOCUMENTS

| | | |
|---|---|---|
| 4,724,232 | 2/1988 | Rideout et al. . |
| 4,921,837 * | 5/1990 | Donahue .................................. 514/2 |
| 5,492,910 | 2/1996 | Barrish et al. . |
| 5,580,769 | 12/1996 | Levy et al. . |
| 5,646,180 * | 7/1997 | Chaturvedi ........................... 514/471 |
| 5,659,045 | 8/1997 | Kempf et al. . |
| 5,665,720 * | 9/1997 | Young et al. ...................... 514/230.5 |
| 5,681,581 | 10/1997 | Dunn . |
| 5,720,952 | 2/1998 | Clark et al. . |

OTHER PUBLICATIONS

Aber et al. The Delta Coordinating Committee; Delta: a randomised double–blind controlled trial comparing combination of zidovudine plus didanosine or zalcitabine with zidovudine alone in HIV–infected individuals; The Lancet; 348; pp. 283–291, 1996.*
Fields, et al. : Fields Virology 3rd Ed.: pp. 446–454, 1996.*
Groopman, et al, "Effect of recombinant human . . . " NEJM 317(10): 593–598, 1987.*
Hammer, et al, "Synergistic activity of . . . " Antimicrob. Agents and Chemotherp. 31(7): 1046–1050, 1987.*
Perno, et al, "Replication of Human . . . " J. Exp. Medicine 169: 933–951, 1989.*
Davey, et al, "A Phase I/II Trial of . . . " J. of Infectious Disease 164: 43–52, 1991.*
Davison, et al, "Qualification of HIV by PCR . . . " J. Clin. Pathol. 47: 855–857, 1994.*
Brites, C. et al., "Granulocyte–macrophage–colony-stimulating factor (GM–CSF) reduces viral load and increases CD4 cell counts in individuals with AIDS," Poster presented to the 38th Interscience Conference on Antimicrobial Agents and Chemotherapy, Sep. 1998.
DiMarzio et al., "GM–CSF or CD40L suppresses chemokine response expression and HIV–entry in human monocytes and macrophages," Abstracts of the 5th Conference on Retroviruses and Opportunistic Infections, p. 86, #37, Feb. 1998.
Hirsch and D'Aquila, "Therapy for human immunodeficiency virus infection," *New England J. of Med,* 328(23):1686–1695, 1993.

New Clinical Data Indicates Leukine Maintains Viral Suppression and Extends Duration of Antiretroviral Therapy Utility in People with AIDS, Immunex Corporation press release, May 3, 1999.
Letter from Steven A. Masiello, Director, Office of Compliance and Biologics Quality, Center for Biologics Evaluation and Research, Federal Drug Administration (Aug. 23, 1999).
Letter from Edward L. Zimney, M.D., Director, Medical Regulatory Affairs, Immunex Corporation (Sep. 7, 1999).
Letter from Steven A. Masiello, Director Office of Compliance and Biologics Quality Center for Biologics Evaluation and Research (Nov. 29, 1999).
Letter from Edward L. Zimney, M.D., Director, Medical Regulatory Affairs, Immunex Corporation (Dec. 22, 1999).
Letter from Steven A. Masiello, Director Office of Compliance and Biologics Quality Center for Biologics Evaluation and Research (Mar. 31, 2000).
Letter from Edward L. Zimney, M.D., Director, Medical Regulatory Affairs, Immunex Corporation (Apr. 19, 2000).
E–mail memorandum from Edward L. Zimney, M.D., Director, Medical Regulatory Affairs, Immunex Corporation (Jun. 23, 2000).
AMFAR (American Foundation for AIDS Research) AIDS/HIV Treatment Directory vol. 7, No. 3, list of clinical trials and study locations, Jun. 1994.
Immunex Annual Report, Product Pipeline, p. 10, 1995.
"Available HIV/AIDS Drugs Update," British Columbia Center for Excellence in HIV/AIDS, St. Paul's Hospital, Vancouver, BC, *Forecast,* Dec. 1995.
"HIV, AIDS and Injection Drug Use: A National Action Plan," British Columbia Center for Excellence in HIV/AIDS, St. Paul's Hospital, Vancouver, BC, *Forecast,* pp. 1 and 7–11, Mar. 1998.
Frumkin, L.R., "Role of granulocyte–stimulating factor and granulocyte–macrophage colony–stimulating factor in the treatment of patients with HIV infection," *Current Opinion in Hematology* 4: 200–206 (1997).
CTN (Canadian HIV Trials Network), University of British Columbia/St. Paul's Hospital, Vancouver, BC, *Network Update,* vol. 6, No. 2, pp. 1–3, Mar./Apr. 1995.
Skowron, G., et al., "Safety and Anti–HIV Effect of GM–CSF in Patients on Highly Active Anti–Retroviral Therapy," 5th Annual Conference on Retroviruses & Opportunistic Infections, Chicago, Illinois, Feb. 1–5, 1998.
Barbaro, G., et al., Effect of recombinant human granulocyte–macrophage colony–stimulating factor on HIV–related leukopenia: a randomized, controlled clinical study, *AIDS* 11:1453–1461, 1997.

(List continued on next page.)

Primary Examiner—Jeffrey Stucker
Assistant Examiner—Ulrike Winkler
(74) *Attorney, Agent, or Firm*—Diana K. Sheiness

(57) ABSTRACT

Provided are methods for reducing the HIV viral load in HIV-infected patients by administering human GM-CSF. The GM-CSF is administered in conjunction with at least two nucleoside reverse transcriptase inhibitors.

14 Claims, No Drawings

OTHER PUBLICATIONS

Bernstein, Z.P., et al., A pilot study in the use of GM–CSF in human immunodeficiency virus (HIV) infected individuals, *Blood* 90 (suppl. 1):133a, 1997.

Delta Coordinating Committee, Delta: a randomised double–blind controlled trial comparing combinations of zidovudine plus didanosine or zalcitabine with zidovudine alone in HIV–infected individuals, *Lancet* 348(9023):283–291, 1996.

Deminie, C.A., Evaluation of reverse transcriptase and protease inhibitors in two–drug combinations against human immunodeficiency virus replication, *Antimicrob Agents Chemother* 40(6):1346–1351, 1996.

Di Marzio, P., et al., Chemokine receptor regulation and HIV type 1 tropism in monocyte–macrophages, *AIDS Res Hu Retrovir* 14(2):129–138, 1998.

Folks, T.M., et al., Cytokine–induced expression of HIV–1 in a chronically infected promonocyte cell line, *Science* 238:800–802, 1987.

Hammer, S.M., et al., In vitro modification of human immunodeficiency virus infection by granulocyte–macrophage colony–stimulating factor and γ interferon, *Proc. Natl. Acad. Sci. USA* 83:8734–8738, 1986.

Hammer, S.M., et al., Effect of zidovudine and granulocyte–macrophage colony–stimulating factor on human immunodeficiency virus replication in alveolar macrophages, *Blood* 75(6):1215–1219, 1990.

Hammer, S.M., et al., A trial comparing nucleoside monotherapy with combination therapy in HIV–infected adults with CD4 cell counts from 200 to 500 per cubic millimeter, *N. Engl. J. Med.* 335(15):1081–1090, 1996.

Hermans, P., et al., Possible role of granulocyte–macrophage colony stimulating factor (GM–CSF) on the rapid progression of AIDS–related Kaposi's sarcoma lesions in vivo, *Br. J. Haematol.* 87:413–414, 1994.

Hermans, P., Haematopoietic growth factors as supportive therapy in HIV–infected patients, *AIDS* 9 (suppl 2):S9–S14, 1995.

Koyanagi, Y., et al., Cytokines alter production of HIV–1 from primary mononuclear phagocytes, *Science* 214:1673–1675, 1988.

Krown, S.E., et al., Interferon–α, zidovudine, and granulocyte–macrophage colony–stimulating factor: a phase I AIDS clinical trials group study in patients with Kaposi's sarcoma associated with AIDS, *J. Clin. Oncol.* 10(8):1344–1351, 1992.

Mochida, K.N. and Rich, E.A., Decreased production of human immunodeficiency virus–1 by granulocyte–macrophage colony–stimulating factor unrelated to promotion of DNA synthesis, ALA/ATS 1998 International Conference, Chicago, Illinois, Apr. 1998, Abstract p. A458.

Perno, C.F. et al., Ability of anti–HIV agents to inhibit HIV replication in monocyte/macrophages or U937 monocytoid cells under conditions of enhancement by GM–CSF or anti–HIV antibody, *AIDS Res Hu Retrovir* 6:1051–1055, 1990.

Perno, C.F. et al., Effects of bone marrow stimulatory cytokines on human immunodeficiency virus replication and the antiviral activity of dideoxynucleosides in cultures of monocyte/macrophages, *Blood* 80:995–1003, 1992.

Rusconi, S., et al., Inhibition of human immunodeficiency virus type 1 replication in cytokine–stimulated monocytes/macrophages by combination therapy, *J. Infect. Dis.* 170:1361–1366, 1994.

Saravolatz, L.D., et al., Zidovudine alone or in combination with didanosine or zalcitabine in HIV–infected patients with the acquired immunodeficiency syndrome or fewer than 200 CD4 cells per cubic millimeter, *N. Engl. J. Med.* 335(15):1099–1106, 1996.

Bender, A., et al., "Effect of granulocyte/macrophage colony–stimulating factor on human monocytes infected with influenza A virus," *J. Immunol.* 151: 5416–5424, 1993.

Crowe, S. and Lopez, A., "GM–CSF and its effects on replication of HIV–1 in cells of macrophage lineage," *J. Leukoc. Biol.* 62: 41–48, 1997.

Davey, R., et al., "A phase I/II trial of zidovudine interferon–α, and granulocyte–macrophage colony–stimulating factor in the treatment of human immunodeficiency virus type 1 infection," *J. Infect. Dis.* 164: 43–52, 1991.

Davison, F., et al., "Quantification of HIV by PCR in monocytes and lymphocytes in patients receiving antiviral treatment and low dose recombinant human granulocyte macrophage colony stimulating factor," *J. Clin. Pathol.* 47: 855–857, 1994.

DiMarzio, P., et al., "Chemokine receptor regulation and HIV type 1 tropism in monocyte–macrophages," *Aids Res. Hum. Retroviruses* 14: 129–138, 1998.

Dorr, R., "Clinical properties of yeast–derived versus *Escherichia coli*–derived granulocyte–macrophage colony–stimulating factor," *Clin. Ther.* 15: 19–29, 1993.

Fletcher, M. and Gasson, J., "Enhancement of neutrophil function by granulocyte–macrophage colony–stimulating factor involves recruitment of a less responsive subpopulation," *Blood* 71: 652–658, 1988.

Foli, A., et al., "Effects of the $Th_1$ and $Th_2$ stimulatory cytokines interleukin–12 and interleukin–4 on human immunodeficiency virus replication," *Blood* 85: 2114–2123, 1995.

Groopman, J., et al., "Effect of recombinant human granulocyte–macrophage colony–stimulating factor on myelopoiesis in the acquired immunodeficiency syndrome," *N. Engl. J. Med.* 317: 593–598, 1987.

Grossberg, H., and Bonnem, E., "GM–CSF with ganciclovir for the treatment of CMV retinitis in AIDS," Abstract *N. Engl. J. Med.*: 1560, 1989.

Hammer, S. and Gillis, J., "Synergistic activity of granulocyte–macrophage colony–stimulating factor and 3'–azido–3'–deoxythymidine against human immunodeficiency virus in vitro," *Antimicrob. Agents Chemother.* 31: 1046–1050, 1987.

Hammer, S., et al., "In vitro modification of human immunodeficiency virus infection by granulocyte–macrophage colony–stimulating factor and γ interferon," *Proc. Natl. Acad. Sci. USA* 83: 8734–8738, 1986.

Hammer, S., et al., "Effect of zidovudine and granulocyte–macrophage colony–stimulating factor on human immunodeficiency virus replication in alveolar macrophages," *Blood* 75: 1215–1219, 1990.

Hardy, D., et al., "Combination of ganciclovir and granulocyte–macrophage colony–stimulating factor in the treatment of cytomegalovirus retinitis in AIDS patients," *Eur. J. Clin. Microbiol. Infect. Dis.* 13: S34–S40, 1994.

Hermans, P., "Haematopoietic growth factors as supportive therapy in HIV–infected patients," *AIDS* 9 Suppl. 2:S9–S14, 1995.

Hermans, P., et al., "Possible role of granulocyte–macrophage colony stimulating factor (GM–CSF) on the rapid progression of AIDS–related Kaposi's sarcoma lesions in vivo," *Br. J. Haematol.* 87(2): 413–414, 1994.

Hewitt, R., et al., "Pharmacokinetics and pharmacodynamics of granulocyte–macrophage colony–stimulating factor and zidovudine in patients with AIDS and severe AIDS–related complex," *Antimicrob. Agents Chemother.* 37: 512–522, 1993.

Hovgaard, D., et al., "Comparative pharmacokinetics of single–dose administration of mammalian and bacterially–derived recombinant human granulocyte–macrophage colony–stimulating factor," *Eur. J. Hematol.* 50: 32–36, 1993.

Kaplan, L., et al., "Clinical and virologic effects of recombinant human granulocyte–macrophage colony–stimulating factor in patients receiving chemotherapy for human immunodeficiency virus–associated non–Hodgkin's lymphoma: results of a randomized trial," *J. Clin. Oncol.* 9: 929–940, 1991.

Koyanagi, Y., et al., "Cytokines alter production of HIV–1 primary mononuclear phagocytes," *Science* 241: 1673–1675, 1988.

Krown, S.E., et al., "Interferon–α, zidovudine, and granulocyte–macrophage colony–stimulating factor: a phase I AIDS clinical trials group study in patients with Kaposi's sarcoma associated with AIDS," *J. Clin. Oncol.* 10: 1344–1351, 1992.

Levine, J., et al., "Recombinant human granulocyte–macrophage colony–stimulating factor ameliorates zidovudine–induced neutropenia in patients with acquired immunodeficiency syndrome (AIDS)/AIDS–related complex," *Blood* 78: 3148–3154, 1991.

Lieschke, G., and Burgess, A., "Granulocyte colony–stimulating factor and granulocyte–macrophage colony–stimulating factor," *N. Engl. J. Med.* 327: 28–35, 1992.

Matsuda, S., et al., "Suppression of HIV replication in human monocyte–derived macrophages induced by granulocyte/macrophage colony–stimulating factor," *Aids Res. Hum. Retroviruses* 11: 1031–1038, 1995.

May, A., et al., "Crystal structure of the N–terminal domain of sialoadhesin in complex with 3' sialyllactose at 1.85 Å resolution," *Mol. Cell* 1: 719–728, 1998.

Miles, S., et al., "Combined therapy with recombinant granulocyte colony–stimulating factor and erythropoietin decreases hematologic toxicity from zidovudine," *Blood* 77: 2109–2117, 1991.

Mitsuyasu, R., "Clinical uses of hematopoietic growth hormones in HIV–related illnesses," *Aids Clin. Rev.:* 189–212, 1993/1994.

Perno, C., et al., "Activity of GM–CSF and M–CSF upon replication of HIV and other DNA– and RNA–viruses in primary macrophages", Program and Abstracts of the $3^{rd}$ Conference on Retroviruses and Opportunistic Infections, Washington, D.C., 1996.

Perno, C., et al., "Replication of human immunodeficiency virus in monocytes," *J. Exp. Med.* 169: 933–951, 1989.

Pluda, J., et al., "Subcutaneous recombinant granulocyte–macrophage colony–stimulating factor used as a single agent and in an alternating regimen with azidothymidine in leukopenic patients with severe human immunodeficiency virus infection," *Blood* 76: 463–472, 1990.

Pluda, J., et al, "Hematologic effects of AIDS therapies," *Hematol. Oncol. Clin. North Am.* 5: 229–248, 1991.

Scadden, D., et al., "Granulocyte–macrophage colony–stimulating factor mitigates the neutropenia of combined interferon alfa and zidovudine treatment of acquired immune deficiency syndrome–associated Kaposi's sarcoma," *J. Clin. Oncol.* 9: 802–808, 1991.

Scadden, D., et al., "Lack of in vivo effect of granulocyte–macrophage colony–stimulating factor on human immunodeficiency virus type 1," *Aids Res. Hum. Retroviruses* 12: 1151–1159, 1996.

Stricker, R. and Goldberg, B., "Increase in lymphocyte subsets following treatment of HIV–associated neutropenia with granulocyte colony–stimulating factor," *Clin. Immunol. Immunopathol.* 79: 194–196, 1996.

Leukine (Sargramostim) A recombinant GM–CSF yeast–expressed, Prodoct Monograph, 1–20.

\* cited by examiner

METHODS FOR TREATING HIV-INFECTED PATIENTS BY ADMINISTERING GM-CSF

FIELD OF THE INVENTION

The subject invention relates to methods for reducing HIV viral load and treating AIDS by administering granulocyte-macrophage colony stimulating factor (GM-CSF).

BACKGROUND OF THE INVENTION

Patients infected with Human Immunodeficiency Virus (HIV) experience a variable but progressive decline in immune function resulting in clinically apparent opportunistic infections and other diseases. (Crowe et al., *J. Acquir. Immune Defic. Syndr.* 4:770–76, 1991; Moss et al., *AIDS* 3:55–61, 1989). The onset of severe immunodeficiency in HIV-infected individuals is generally accompanied by a marked increase in viral burden and a dramatic decline in circulating $CD4^+$ T-lymphocytes. Recent approaches to HIV therapy include administration of immunomodulatory agents, such as interleukin-2, with antiretroviral drugs to improve host immunity, thereby attempting to decrease opportunistic infections and prolong survival. Cytokines and growth factors may have a beneficial effect by increasing the number and function of immune system effector cells, including neutrophils, monocytes, macrophages, lymphocytes, dendritic cells, and natural killer cells; however, there is some concern that activation of lymphocytes or monocytes/macrophages may potentially increase the HIV load and produce toxicity that limits the use of these biologics. Indeed, decrease in viral burden is one of the primary clinical end-points for halting the progression of HIV infection. Accordingly, a decrease in viral load is generally regarded as an indicator of efficacy for anti-HIV drugs.

Inhibition of HIV replication can reduce viral load. Such antiretroviral therapy typically involves combinations of drugs such as protease inhibitors, nucleoside analogs, and non-nucleoside reverse transcriptase inhibitors. Other agents, including biologics, have also demonstrated some antiviral effects. The decrease in viral load is generally, but not always, associated with an increase in the number of circulating $CD4^+$ T-cells. (Yarchoan et al., *Ann Intern. Med.* 115:184–89, 1991; Hirsch and D'Aquila, N. *Engl. J. Med.* 328:1686–95, 1993; Volberding, P. A., In: Crowe et al., eds., *Management of the HIV-Infected Patient*, pp. 53–63). Unfortunately, antiretroviral drugs do not result in complete reconstitution of the immune function. Moreover, inhibition of viral replication by these agents is temporary, due to the evolution of resistant strains of virus that can grow in the presence of the antiretroviral agents. (Cameroni et al., Third Human Retroviral Conference, January 1996, Abstract #LB6a).

Growth factor cytokines such as granulocyte-colony stimulating factor (G-CSF), granulocyte-macrophage colony stimulating factor (GM-CSF), and erythropoietin (EPO) have also been administered to patients with HIV. (Scadden et al., 1991, Levine et al., *Blood* 73:3148–54, 1991; Kaplan et al., *J. Clin. Oncol.* 9:929–40, 1991; Stricken and Goldberg, *Clin. Immunol. Immunopathol.* 79:194–96, 1996; Miles et al., *Blood* 77:2109–17, 1991; Pluda et al., *Hematol. Oncol. Clin. North Am.* 5:22948, 1991). Recently, GM-CSF has been the subject of several studies to evaluate its ability to prevent opportunistic infections in individuals with HIV.

LEUKINE®, a yeast-derived form of GM-CSF, is currently available for use in promoting myeloid cell recovery following bone marrow transplant post-myeloablative therapy for the treatment of malignancies. An *E. coli*-derived form of GM-CSF is also available for use in promoting the recovery of neutrophils in HIV-infected patients with granulocytopenia. (Scadden et al., *J. Clin. Oncol.* 9:802–08, 1991; Levine et al., Blood 78:3148–54, 1991; Kaplan et al., *J. Clin. Oncol.* 9:929–40, 1991; Hardy et al., Eur. *J. Clin. Microbiol. Infect. Dis.* 13:S34-S40, 1994). However, the widespread use of GM-CSF for treatment of HIV infection has been hindered by data from in vitro studies whose results suggest that this cytokine might actually enhance HIV replication (Bender et al., *J. Immunol.* 151:5416, 1993; Foli et al., *Blood* 8:2114, 1995; Pluda et al., *Hematol. Oncol. Clin. North Am.* 5:229–48, 1991). More recent studies have reported results which are inconsistent with earlier studies with regard to the effect of GM-CSF on HIV viral replication (Perno et al., Third Human Retroviral Conf., January 1996, Abstract #463; Pluda et al., Blood 76:463–72, 1990; Fletcher and Gasson, *Blood* 71:652–58, 1988; Mitsuyasu, R. T. In: Volberding and Jacobson, eds. *AIDS Clinical Review*, N.Y., N.Y. 1993–94, pp. 189–212). It is now believed that in the presence of antiretroviral therapy, GM-CSF does not increase HIV viral replication. (Scadden et al., 1995; Davison et al., *J. Clin. Pathol.* 47:855–57, 1994, Scadden et al., *AIDS Res. and Human Retroviruses* 12:1151–59, 1996). Indeed, in vitro data have demonstrated the enhancement of AZT activity by GM-CSF due to increased intracellular concentration of the active triphosphorylated form of AZT. (Hammer and Gillis, *Antimicrob. Agents Chemother.* 31:1046–50, 1987).

Developing effective therapies for HIV disease has presented a formidable challenge for medical researchers. Although significant advancements have been made in the treatment of HIV-infected patients, many patients remain untreatable due to ineffectiveness of the therapeutic drugs used or inability of the patients to tolerate the side effects of the therapies. Clearly, existing therapies do not yet offer a cure to HIV disease. Immune-modulating agents, such as GM-CSF, may therefore offer an additional alternative treatment.

SUMMARY OF THE INVENTION

The present invention is directed to the discovery that GM-CSF is capable of reducing viral load in HIV-infected patients. The present invention is therefore directed to methods for reducing HIV viral load in HIV-infected patients by the therapeutic administration of GM-CSF. This method of treatment has been demonstrated to reduce the HIV viral load in patients concurrently receiving antiretroviral drugs.

This invention is based on the results of double-blinded, placebo-controlled studies that enrolled HIV-infected patients at multiple study sites. Patients receiving anti-retroviral agents received therapeutically effective amounts of recombinant human GM-CSF or placebo. Viral load and $CD4^+$ T-lymphocyte counts were determined prior to the start of the study (baseline), then at intermittent periods after the start of the study. Results indicated that GM-CSF caused a clinically significant reduction in the HIV viral load in a significantly greater number of individuals.

DETAILED DESCRIPTION OF THE PREFERRED EMBODIMENT

The present invention provides methods for reducing HIV viral load in an HIV-infected patient by administering therapeutically effective amounts of granulocyte-macrophage colony stimulating factor (GM-CSF).

In accordance with the present invention, GM-CSF is administered to HIV-infected patients in amounts and for a time sufficient to induce a significant decrease in HIV viral load. "HIV viral load" is measured by determining the level of HIV-RNA (measured in copies per ml) detectable by PCR in the plasma of an HIV-infected patient. For the purposes of the present invention, a "clinically significant" reducation in HIV viral load is defined as a reduction greater than or equal to about 0.5 $\log_{10}$ relative to the baseline value.

GM-CSF used in the practice of the invention includes any pharmaceutically safe and effective human GM-CSF, or any derivative thereof having the biological activity of human GM-CSF. In a presently preferred embodiment, the GM-CSF used in the practice of the subject methods is recombinant human GM-CSF (rhu GM-CSF), such as LEU-KINE® (Immunex Corporation, Seattle, Wash.). LEUK-INE® is a biosynthetic, yeast-derived, recombinant human GM-CSF, consisting of a single 127 amino acid glycoprotein that differs from endogenous human GM-CSF by having a leucine instead of a proline at position 23. Other natural and synthetic GM-CSFs, and derivatives thereof having the biological activity of natural human GM-CSF, may be equally useful in the practice of the invention.

As the degree of glycosylation of biosynthetic GM-CSFs appears to influence half-life, distribution, and elimination, the most effective dose of GM-CSF for the subject methods may vary depending on the source used (Lieschke and Burgess, *N. EngL. J. Med.* 327:28–35, 1992; Dorr, R. T., *Clin. Ther.* 15:19–29, 1993; Horgaard et al., *Eur. J. Hematol.* 50:32–36, 1993). The optimal dose of GM-CSF used for LEUKINE® may be adjusted if a GM-CSF other than LEUKINE® is used to reduce the HIV viral load in HIV-infected patients.

LEUKINE® has been shown to exhibit the same hemato-poietic effects as those induced by endogenous GM-CSF, namely, the stimulation of progenitor cells committed along the granulocyte-macrophage pathway to form neutrophils, monocytes, macrophages, and eosinophils (Technical Product Report: LEUKINE® Liquid, Immunex Corp., Seattle, Wash., 1997, which is herein incorporated by reference). LEUKINE®, like endogenous GM-CSF, also promotes the differentiation of progenitor cells giving rise to erythrocytes and megakaryocytes (Ibid.) In addition to stimulating hematopoiesis, LEUKINE® enhances many of the functional activities of mature neutrophils, monocytes and macrophages, such as chemotaxis, growth factor secretion, anti-tumor activity, antibacterial and antifungal activities, and so on (Ibid.).

Various embodiments of the subject invention are disclosed herein. In one preferred embodiment, GM-CSF may be administered concurrently with antiretroviral agents, including, but not limited to, nucleoside reverse transcriptase inhibitors, non-nucleoside reverse transcriptase inhibitors, or protease inhibitors. The term "antiretroviral agent", as used herein, includes any pharmacological, biological or cellular agent that has demonstrated the ability to inhibit HIV replication. Specific examples of nucleoside reverse transcriptase inhibitors include zidovudine (AZT), didanosine (ddI), lamivudine (3TC), stavudine (d4T), and dalcitabine (ddC). Specific examples of non-nucleoside reverse transcriptase inhibitors include nevirapine and delavirdine. Specific examples of protease inhibitors include indinavir, nelfinavir, ritonavir, and saquinavir. Patients treated in accordance with the present invention may be treated concurrently with one or more anti-retroviral agents. Additional antiretroviral agents not yet approved by the Food and Drug Administration may also be effective.

The optimal dose, frequency of administration, and duration of treatment with GM-CSF which is effective to induce a clinically significant decrease in HIV viral load may vary from patient to patient. Generally, however, therapeutically effective doses of GM-CSF sufficient to induce a decrease in HIV viral load will be greater than or equal to about 100 micrograms (mcg). Preferably, doses of GM-CSF will be greater than or equal to about 125 mcg, and more preferably, doses of GM-CSF will be greater than or equal to about 150 mcg. Most preferably, doses of GM-CSF will be greater than or equal to about 125 mcg/m$^2$.

In preferred embodiments of the present invention, GM-CSF is administered for a period of time greater than about three weeks, and more preferably greater than about four weeks, at a frequency of at least two times per week, more preferably at least three times per week. GM-CSF may also be administered more frequently, for example, once per day or more. However, it should be understood that the optimal dose and length of treatment may vary from patient to patient, depending on the individual patient's condition and response to the treatment, and is best determined by monitoring the patient's response during the course of the treatment. It should further be understood that administration of higher doses may permit less frequent administration, and lower doses may require more frequent administration in order to achieve a clinically significant reduction in HIV viral load. A treatment regimen (dosage amount, frequency and duration) is therapeutically effective if it results in a clinically significant decrease in HIV viral load.

The methods of the subject invention thus include reducing HIV viral load in an HIV-infected patient who may also be treated with an antiretroviral agent in which the patient is administered an amount of GM-CSF sufficient to induce a decrease in HIV viral load.

EXAMPLE 1

GM-CSF Reduces Viral Load in HIV-Infected Patients

A study was conducted to determine the safety and efficacy of human GM-CSF (Leukine©) as a therapeutic reagent in HIV-infected patients. Because some in vitro studies had indicated the possibility that GM-CSF might enhance HIV replication in vivo, this study assessed the impact of co-administration of GM-CSF with an antiretroviral agent on HIV replication. HIV viral burden was measured by the RNA-PCR (Amplicor®) method. To assess the effects of this treatment on lymphocyte counts, blood samples were analyzed throughout the study for determination of CD3$^+$, CD4$^+$, and CD8$^+$ T-lymphocyte counts.

This study was a Phase I/II, randomized, double-blind, placebo-controlled, two-center trial involving patients with HIV disease. Patients meeting specific entry criteria were randomized to treatment with GM-CSF or placebo, and these were administered by subcutaneous injection three times per week for eight weeks. Viral load was determined at baseline (mean of three determinations within fourteen days of study entry), then at two weeks, four weeks, and eight weeks after starting study drugs, and on two separate occasions approximately four weeks after the conclusion of the treatment phase (post-treatment evaluation). Clinical, viral load and lymphocyte subset evaluations were performed at each of these same time points (i.e., pre-treatment, week 2, week 4, week 8, and 4 weeks post-study). Twenty patients were enrolled in the study, ten per treatment arm. All twenty patients completed the study.

Patients were eligible for inclusion in the study if the following parameters were met: documented HIV infection, including detectable RNA-PCR during baseline evaluation period, age $\geq 18$ years (or legal age of consent), adequate hematologic function, satisfactory hepatic and renal function, adequate clinical performance status, treatment with an antiretroviral regimen that included either ritonavir or indinavir for at least 8 weeks prior to study enrollment and agreement to continue on a stable regimen throughout the study, ability and willingness to provide written informed consent, agreement to practice medically-approved contraception.

Patients were ineligible for inclusion in the study if the following exclusion criteria were met: concurrent pregnancy or breast feeding, concurrent use of other colony stimulating factors or cytokines (other than erythropoietin), life-expectancy <90 days, concurrent radiation or systemic cancer chemotherapy (or within 2 weeks prior to study entry), inability to self-administer or arrange for administration of subcutaneous injections, significant cardiac disease, prior history of adverse reaction to yeast-derived rhu GM-CSF which would prohibit retreatment, active infection (AIDS-related or not) requiring acute systemic therapy within 8 weeks prior to study enrollment, vaccination of any kind within 8 weeks of study enrollment.

Study participants were randomly assigned to receive either active GM-CSF or placebo. Patients were instructed in methods for self-administration of study medication and received preloaded syringes or vials with empty syringes for home use.

The formulation of recombinant human GM-CSF utilized in this clinical trial was LEUKINE® (commercially available from Immunex Corporation, Seattle, Wash.). LEUKINE® and placebo were supplied as lyophilized powders. Both LEUKINE® and placebo were reconstituted by the aseptic injection of Bacteriostatic Water for Injection, USP, containing 0.9% benzyl alcohol. The placebo control for the subject study was a sterile lyophilized preparation containing only the inactive excipients present in the LEUKINE® preparation. These were 40 mg mannitol, USP; 10 mg sucrose, NF; and 1.2 mg TRIS (tromethamine), USP; per vial of study drug. Vials containing placebo were labeled in a fashion identical to vials containing LEUKINE®. Vials of placebo and LEUKINE® were stored refrigerated at 2–8° C. (36–46° F.).

Patients assigned randomly to treatment Group I received blinded subcutaneous injections of active reconstituted lyophilized LEUKINE® in a fixed dose of 250 mcg in a volume of 0.5 mL three times per week for eight weeks (24 doses), while patients assigned to treatment Group II received blinded subcutaneous injections of 0.5 mL of the placebo according to the same schedule. Safety evaluations included monitoring of HIV viral load by sensitive RNA-PCR methods and clinical monitoring for HIV-related illnesses.

At 2, 4 and 8 weeks after the start of study drug and at follow-up (approximately 4 weeks after completion of study drug), patients were examined, their medical histories were updated, and samples were taken for laboratory studies. A central laboratory was utilized for HIV quantification laboratory tests in order to standardize procedures and minimize variability. These samples were batched by subject to further reduce variability and, with exception of the screening RNA-PCR, results were not available to the study site until after the completion of the study. All other laboratory evaluations were analyzed at licensed laboratories near the study site. Samples for these other tests were drawn at screening, baseline (pre-treatment), week 2, week 4, week 8, and 4 weeks post-discontinuation. These other laboratory evaluations included: Complete blood count (CBC) with differential, platelet count, serum chemistries (electrolytes, blood urea and nitrogen (BUN), creatinine, bilirubin, aspartate amino transaminase (AST), alkaline phosphatase), CD3/CD4/CD8 lymphocyte absolute counts and percentage of total lymphocytes. Additionally, plasma was saved for future cytokine analyses. A single urinalysis was done at baseline to document eligibility.

The results of the study are summarized in the following table, showing both placebo treatment and GM-CSF treatment. The mean change in viral load of the evaluable group was negative for all patients receiving GM-CSF and the 95% confidence interval excluded a 0.5 $\log_{10}$ increase in HIV load relative to baseline. (Patients with baseline HIV loads below or above the limits of detection or which varied by >1.0 $\log_{10}$ were excluded from the analysis.)

| | Log Change in HIV Viral Load from Baseline | | |
|---|---|---|---|
| | Placebo (n = 8) | GM-CSF (n = 7[1]) | |
| | Mean (SD) change from baseline | Mean (SD) change from baseline | 95% confidence change from baseline |
| Week 2 | −0.03 (0.21) | −0.16 (0.42) | (−0.55, 0.23) |
| Week 4 | 0.08 (0.36) | −0.15 (0.37) | (−0.49, 0.19) |
| Week 8 | 0.22 (0.36) | −0.01 (0.45) | (−0.43, 0.41) |
| Follow-up 1 (week 12) | 0.23 (0.77) | −0.21 (0.48) | (−0.71, 0.29) |
| Follow-up 2 | 0.07 (0.49) | 0.06 (0.25) | (−0.20, 0.32) |
| Maximum Increase | 0.52 (0.49) | 0.23 (0.23) | (0.02, 0.44) |
| Maximum Decrease | −0.36 (0.32) | −0.44 (0.38) | (−0.79, −0.09) |

[1] n = 6 for follow-up 1 and 2 due to exclusion of one subject for protocol violations This data shows that the decrease in viral load at week 12 was significantly greater for GM-CSF-treated patients (−0.21 $\log_{10}$ change), compared to placebo-treated patients (+0.23 $\log_{10}$ change) who showed a mean increase in viral load.

As an additional indicator of efficacy, the proportion of HIV-RNA values $\geq 0.5$ $\log_{10}$ decrease from baseline was calculated. In the placebo group, only 1/8 subjects and 1/40 measurements showed a decrease of HIV-RNA $\geq 0.5$ $\log_{10}$, while in the GM-CSF group 4/7 subjects and 7/33 measurements showed a decrease of $\geq 0.5$ $\log_{10}$. Thus, the frequency of a $\geq 0.5$ $\log_{10}$ decrease in viral load was significantly higher in the GM-CSF group compared to the control group (p=0.019).

EXAMPLE 2

GM-CSF Reduces Viral Load in AIDs Patients

To determine the effect of GM-CSF on viral load and the incidence of opportunistic infections, 105 HIV-infected individuals were randomized to receive AZT at a dose of 300 mg/day and either 125 mcg/m$^2$ of yeast derived GM-CSF (LEUKINE®) or an identically-appearing placebo administered by subcutaneous injection two times per week for twenty-six weeks. Viral load, as measured by HIV-RNA PCR (NASBA, Organon Teknika), and lymphocyte subset evaluations (CD4$^+$ and CD8$^+$) were performed at baseline, and at 1 month, 3 months and 6 months after starting study drugs. Other laboratory evaluations (hematologies and serum chemistries) were performed monthly throughout the study. Clinical evaluations were performed on a weekly basis.

Patients were eligible for inclusion in the study if the following parameters were met: documented HIV infection, age 18–50 years, CD4+ cell count at baseline <300 cells/cmm, AIDS diagnosis within 3 months of study enrollment, Karnofsky performance status of ≧60%, adequate hematologic, hepatic and renal function, ability and willingness to provide written informed consent, and ability and willingness to comply with the study procedures. Patients were ineligible for inclusion in the study if the following exclusion criteria were met: prior use of any immunomodulators or antiretroviral agents other than AZT, prior use of AZT for >6 months, active infection (AIDS-related or not) at the time of study enrollment, presence of malignant diseases (except Stage I Kaposi's sarcoma), diagnosis of AIDS Dementia Complex, concurrent pregnancy or breast feeding. Patients were allowed to receive newer antiretroviral agents as they became available, but AZT maintenance was required throughout the study. Seventy of the subjects received additional antiretroviral agents at some time during the study.

Study drug (GM-CSF or Placebo) was supplied, stored and prepared in a similar manner to that described in Example 1. Study drug was administered by medical personnel at the participating research institutions.

Two central laboratories were utilized for HIV quantification in order to standardize procedures and minimize variability. The viral load samples were batched by subject to further reduce variability. Results were not available to the study site until after the completion of the study. All other laboratory evaluations were analyzed at licensed laboratories near the study site.

Statistically, no differences between groups were observed in baseline viral load, prior opportunistic infections, and the use of additional nucleoside analogs. Baseline CD4+ cell counts were significantly lower in the GM-CSF group compared to the placebo group (median 80 cells/$\mu$l v. 137 cells/$\mu$l; p=0.029).

A preliminary interim analysis of the first 15 patients revealed that the GM-CSF-treated group showed greater reductions from baseline in HIV viral load within 10 weeks of baseline. Mean changes from baseline were $-0.40$ $\log_{10}$ for the GM-CSF group and $-0.29$ $\log_{10}$ for the placebo group.

A subsequent interim analysis on the first 66 patients indicated significantly greater decreases in HIV viral load in patients receiving GM-CSF. At 1 month the median changes in viral load from baseline were $-0.06$ $\log_{10}$ for placebo and $-0.03$ $\log_{10}$ for GM=CSF (p=0.03).

For the full study of 105 patients, median changes in viral load from baseline were $-0.03$ $\log_{10}$ for placebo and $-0.15$ $\log_{10}$ for GM-CSF at 1 month (p=0.14), 0.00 $\log_{10}$ for placebo and $-0.33$ $\log_{10}$ for GM-CSF at 3 months (p=0.06), and $-0.01$ $\log_{10}$ for placebo and $-0.51$ $\log_{10}$ for GM-CSF at 6 months (p=0.02). The GM-CSF group, relative to placebo, also had a significantly greater number of individuals with $\geq 0.5$ $\log_{10}$ reduction in virus at multiple measurements (33% v. 17%; p=0.10) and $\geq 1.0$ $\log_{10}$ reductions in virus (43% v. 16%; p<0.01). These data demonstrate that the GM-CSF group showed significant reductions in viral load at both 3 and 6 months.

Analysis of the minimum and maximum reductions in viral load also demonstrate that GM-CSF had a significant impact on the maximum viral loads of patients. Among the placebo group, changes in viral loads at 6 months ranged from a minimum of $-2.89$ $\log_{10}$ to a maximum of 3.33 $\log_{10}$, indicating a wide variety of responses. In contrast, viral loads at 6 months among the GM-CSF group ranged from a minimum of $-3.59$ $\log_{10}$ to a maximum of 0.95 $\log_{10}$, indicating a significant reduction in the maximum viral loads. This indicates that GM-CSF significantly reduces the number of patients who experience an increase in viral load.

A further indicator that GM-CSF significantly reduced viral load was the number of patients whose viral load was reduced to undetectable levels. In the placebo group only 2 of 49 patients (4%) experienced reductions in viral load to undetectable levels, and in the GM-CSF group 5 of 46 patients (11%) experienced reductions in viral load to undetectable levels. This demonstrates that GM-CSF is more effective than placebo in reducing viral loads to levels considered effective in treating AIDs.

Change in absolute CD4+ cell count ($\Delta$CD4+) was consistent with the above conclusions, being higher in the GM-CSF group at each time point, and with significantly more individuals having $\geq 30\%$ increase in CD4+ cell count at any time on therapy (80% v. 58%; p=0.027).

While the preferred embodiment of the invention has been illustrated and described, it will be appreciated that various changes can be made therein without departing from the spirit and scope of the invention.

I claim:

1. A method for treating an HIV-infected patient, consisting of concurrent administration of two or more nucleoside reverse transcriptase inhibitors and human granulocyte-macrophage colony stimulating factor (GM-CSF) in amounts and for a time sufficient to induce a clinically significant reduction in HIV viral load.

2. The method of claim 1, wherein the GM-CSF is human recombinant GM-CSF.

3. The method of claim 2, wherein the GM-CSF is administered for a time greater than three weeks.

4. The method of claim 3, wherein the GM-CSF is administered at least two times per week.

5. The method of claim 4, wherein the GM-CSF is administered at a dose of greater than or equal to about 100 mcg.

6. The method of claim 4, wherein the GM-CSF is administered three times per week.

7. The method of claim 1, wherein the amount of GM-CSF administered is at least 125 mcg per dose.

8. The method of claim 1, wherein the nucleoside reverse transcriptoae inhibitors and GM-CSF are administered for a period of time greater than or equal to about four weeks.

9. The method of claim 8, wherein the period of time is greater than three months.

10. The method of claim 9, wherein the period of time is greater than six months.

11. The method of claim 1, wherein one of the nucleoside reverse transcriptase inhibitors is AZT.

12. The method of claim 1, wherein the GM-CSF is recombinant GM-CSF.

13. The method of claim 1, wherein the GM-CSF is administered at least two times per week.

14. The method of claim 13, wherein the GM-CSF is administered three times per week.

* * * * *